United States Patent [19]

Molnar et al.

[11] Patent Number: 5,082,835
[45] Date of Patent: Jan. 21, 1992

[54] NOVEL STEROID DIOLS, PHARMACEUTICAL COMPOSITIONS CONTAINING THEM AND PROCESS FOR PREPARING SAME

[75] Inventors: Csaba Molnar; György Hajos; Laszlo Szporny; Jozsef Toth; Arpad Kiraly; Anna Boor nee Mezei; Janos Csörgei; Kristina Szekely; Lilla Forgacs; György Fekete; Bulcsu Herenyi; Sandor Holly; Jozsef Szunyog, all of Budapest, Hungary

[73] Assignee: Richter Gedeon Vegyeszeti Gyar R.T., Budapest, Hungary

[21] Appl. No.: 491,683

[22] Filed: Mar. 9, 1990

[30] Foreign Application Priority Data

Mar. 9, 1989 [HU] Hungary ............................. 1156/89

[51] Int. Cl.$^5$ ................................. C07J 7/00
[52] U.S. Cl. ................................. 514/180; 514/181; 552/566
[58] Field of Search ................. 514/180, 181; 552/566

[56] References Cited

U.S. PATENT DOCUMENTS 3,167,545  1/1985  Rosenkranz et al. ............. 540/63
3,345,362  10/1987  Rapala .......................... 540/63

OTHER PUBLICATIONS

J. Chem. Soc. pp. 4383–4388 (1955).
J.A.C.S., 95 No. 9, pp. 2865–2868 (1973).
Acta Cryst., 834, pp. 3027–3036 (1978).
International Symposium on Molecular Recognition, Its Role in Chemistry and Biochemistry, SOPRON, 1988, W. L. Duax et al.
4th Symposium on the Analysis of Steroids, PECS, 1990, Duax, W. L. et al., (1990), The Stereochemical Aspects of Receptor Binding Steroids.

Primary Examiner—Mukund J. Shah
Assistant Examiner—E. C. Ward
Attorney, Agent, or Firm—Herbert Dubno; Jonathan Myers

[57] ABSTRACT

The invention relates to antiinflammatory compounds of the formula (I),

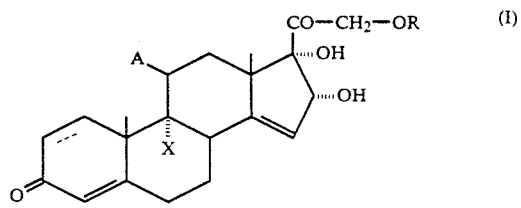

wherein
A stands for hydrogen, hydroxyl or trifluoroacetoxy group;
X stands for hydrogen or halogen with the proviso that if A is hydrogen, then X also means hydrogen;
R stands for hydrogen, benzoyl or $C_{1-8}$alkanoyl group; and
 represents a single or double bond between two adjacent carbon atoms, as well as pharmaceutical compositions containing these compounds and a process for their preparation.

6 Claims, No Drawings

NOVEL STEROID DIOLS, PHARMACEUTICAL COMPOSITIONS CONTAINING THEM AND PROCESS FOR PREPARING SAME

The invention relates to novel $\Delta^{14}$-16α,17-dihydroxy-pregnane derivatives of the formula (I),

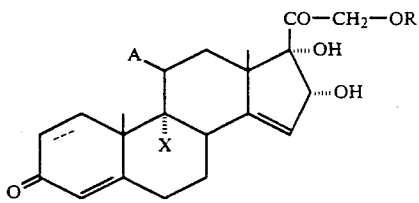

wherein
- A stands for hydrogen, hydroxyl or a trifluoroacetoxy group;
- X stands for hydrogen or halogen with the proviso that if A is hydrogen, then X also means hydrogen;
- R stands for hydrogen, benzoyl or $C_{1-8}$alkanoyl group; and
- represents a single or double bond between two adjacent carbon atoms, pharmaceutical compositions containing a physiologically effective dose of these compounds and process for preparing these compounds and compositions. Furthermore, the invention relates to a method of treatment, which comprises using these compounds or compositions.

The novel $\Delta^{14}$-16α,17-dihydroxypregnane derivatives of the formula (I)

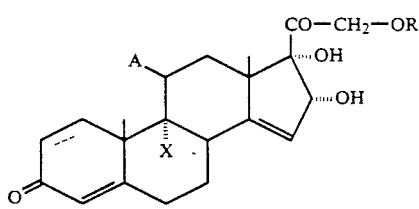

according to the invention posses valuable antiinflammatory activity and therefore they can be used as active ingredients in pharmaceutical compositions and, on the other hand, they can be employed for the preparation of other steroid derivatives similarly possessing therapeutic effects.

Throughout this description the term halogen is meant to include fluorine, chlorine, bromine or iodine, preferably fluorine or chlorine; $C_{1-8}$alkanoyl means formyl, acetyl, propionyl or any of the various butyryl, valeryl, hexanoyl, heptanoyl or octanoyl groups; in addition to the above groups acyl includes a benzoyl group, too. $C_{2-4}$alkanoic acids mean acetic, propionic, n- and isobutyric acid.

Throughout this description and in the claims alkali metal defines lithium, sodium and potassium or their cations, respectively, as well as ammonium cation possessing similar characteristics. Preferable alkali metals are sodium and potassium. Alkaline earth metals include magnesium, calcium, strontium and barium.

It is known (L. Fieser and M. Fieser: Steroids, Reinhold Publ. Co., page 650, 1967) that patients suffering from rheumatoid arthritis have successfully been cured with cortisone as early as 1949. However, treatments widely carried out with cortisone or hydrocortisone, respectively, have soon shown that native corticosteroids induced a number of undesired (unwanted) side effects in addition to the desired antiinflammatory effect. (Such harmful side effects were: salt and water household disorders, water retention, osteoporosis, recrudescence of healed gastric ulcers and the like.)

Several modifications were made on the structure of cortisone and hydrocortisone to eliminate these side effects and increase the desired antiinflammatory action.

These research works resulted e.g. in the discovery of prednisolone, triamcinolone, dexamethasone, fluocinolone acetonide as well as novel 3-chloropregnane derivatives (see the Hungarian patent specification No. 182,775). The role of these drugs has not been diminished in modern therapy up to the present.

In the course of our synthetic work oriented to derivatives having more favorable effects in comparison with those of the known ones it has been found that the novel $\Delta^{14}$-16α,17-dihydroxypregnane derivatives of the formula (I)

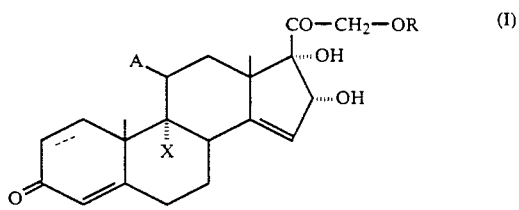

exert a favorable antiinflammatory action and/or they can be used as starting substances for the preparation of other highly effective antiinflammatory corticoids.

According to an other aspect of the invention, there is provided a process for the preparation of the new compounds of the formula (I)

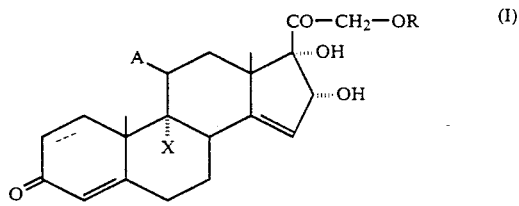

which comprises oxidizing a pregnane derivative of the formula (II)

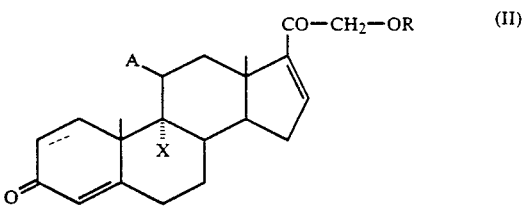

wherein A, X and the symbol (bond line)   are as defined above and R is as defined above except hydrogen, with an alkaline metal permanganate or alkaline earth metal permanganate in a $C_{2-4}$alkanoic acid medium in the presence of water and optionally acetone; then, if desired, hydrolyzing a thus obtained $\Delta^{14}$-16α,17-dihydroxypregnane derivative of formula (I) wherein A, X and the symbol (bond line)   are as defined above and R stands for an acyl group to obtain a compound of the formula (I)

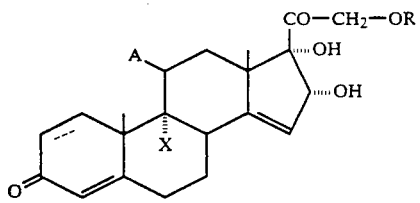

wherein R stands for hydrogen.

In the course of the process according to the invention, the introduction of hydroxyl groups into 16α- and 17-positions as well as the $\Delta^{14}$ double bond formation proceed in a single-step reaction in the compounds of the formula (II) containing the $\Delta^{16}$ double bond. This transformation is surprising since no transformation of this kind has been described in the theoretical literature discussing the oxidation of unsaturated bonds with permanganate. A similar transformation has only been reported in a single literature reference (J. Chem. Soc. 1955, 4383) where the oxidation of 3β-acetoxypregna-5,16-dien-20-one was discussed; it has been stated that in the course of the oxidation, besides 3β-acetoxy-16α,17α-dihydroxypregn-5-en-20-one, its 14,15-dehydro derivative was also formed as a result of a side reaction. The yield of the side product was low and not discussed in detail in the above paper.

According to a preferred embodiment of the process of the invention the pregnane derivative of the formula (II)

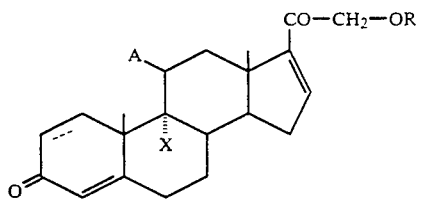

used as starting substance is conveniently dissolved either in a mixture of acetic acid and acetone or in glacial acetic acid; then an aqueous potassium permanganate solution is portionwise added to the above solution at a temperature below 0° C. (suitably at a temperature between −20° C. and −25° C.) in case of using a mixture of acetic acid and acetone or at a temperature of about 10° C. in case of using glacial acetic acid. The aqueous potassium permanganate solution is used in an excess of 0.8 to 1.0 mole calculated for the steroid compound. This reaction proceeds within a period of 5 to 30 minutes depending on the starting substance used. During this period the temperature of the mixture is kept constant. After termination of the reaction the mixture is poured into water to precipitate the $\Delta^{14}$-16α,17-dihydroxypregnane derivatives of the formula (I)

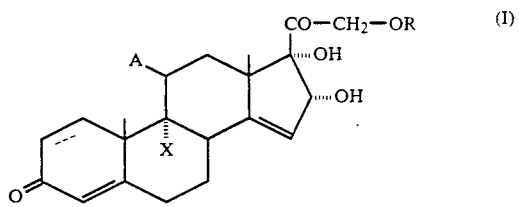

wherein R stands for $C_{1-8}$alkanoyl group or benzoyl group.

The thus obtained products of the formula (I)

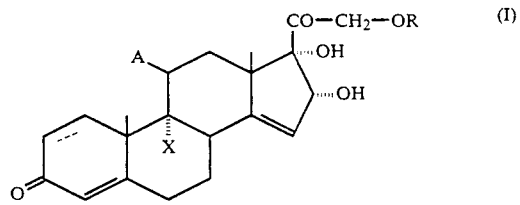

wherein R is $C_{1-8}$alkanoyl or benzoyl group can be hydrolyzed by dissolving in a protic solvent, e.g. methanol and treating with an aqueous alkaline metal carbonate or, suitably, with aqueous perchloric acid solution.

The $\Delta^{14}$-16α,17-dihydroxypregnane derivatives of formula (I)

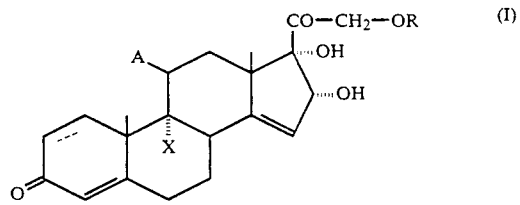

according to the invention possess valuable glucocorticoid effects.

Two principal (essential) demands are set up against topically used steroid antiinflammatory drugs: a) they should be as active as possible in various animal experiments used for investigating the antiinflammatory action; and b) they should induce the lowest harmful systemic side effect. This latter effect can be well characterized by the thymus weight-decreasing action (involution).

The tests used for investigation of the anti-inflammatory action of the compounds according to the invention are described hereinafter. Prednisolone (11β,17α,21-trihydroxypregna-1,4-dien-3,20-dione) was used as a reference drug in these tests.

1) The oxazolone-induced contact dermatitis model [Br. J. Pharmac. 43, 403 (1971)]

Male CFLP mice weighing 20 to 24 g each were used in this test. The abdominal skin of the animals was shaved and 0.1 ml of a 2% oxazolone solution in olive oil was applied onto the skin. Seven days following this treatment an inflammation response was elicited by applying 10 μl of a 2% oxazolone solution in acetone onto the left ears of the animals. The right ears were used as control. After 24 hours the ears of the animals were cut off and weighed. On investigation of the test compounds, the substance under test was added in various concentrations to the acetone solution containing oxazolone. For evaluation the diminution of the ear weight increase was expressed as "percentage of inhibition" in comparison to the control treated with no active agent. Ten mice were used in each group.

2) The local granuloma sac model

[Recent Progr. Hormone Res. 8, 117 (1953); Arzneim.-Forsch. 27, 11 (1977)].

This method was used to investigate the anti-exudative action of the topically administered glucocorticoids. The systemic side effect (thymus involution) was observed on the same experimental animals.

Groups consisting of 10 female RG Hann Wistar rats each weighing 130 to 150 g were used. After shaving the back of the animals 25 ml of air were injected beneath the back skin and 1 ml of 2% croton oil inducing inflammation was introduced to the air sac. After 5 days the content of the sac was removed by suction and once 3 doses each of the glucocorticoids to be tested or prednisolone, respectively, in a volume of 0.5 ml suspension in Tween 80 were administered by an injection syringe. On the 10th day following the start of the experiment the animals were sacrificed and the exudate liquid of the sac (expressed as ml) was measured. The percentage of the antiinflammatory effect was calculated based on the decrease in the volume of exudate related to that of the control.

Then, the thymi of the animals were excised and the harmful systemic side effect of the test compounds was calculated as a percentage based on the comparison of the thymus weight of animals treated with the test compounds to that of the untreated control group.

The above investigations gave the following results.

| Antiinflammatory effect on the oxazolone-induced contact dermatitis model | | | |
| --- | --- | --- | --- |
| Compound | Dose (μg/ear) | Ear weight increase (%) | Inhibition (%) |
| Control | 0 | 108.8 | 0 |
| Prednisolone | 0.3 | 86.1 | 20.8 |
| Prednisolone | 1.0 | 76.9 | 29.3 |
| Prednisolone | 3.0 | 68.6 | 36.9 |
| Example No. 3 | 0.3 | 86.2 | 20.8 |
| Example No. 3 | 1.0 | 75.5 | 30.6 |
| Example No. 3 | 3.0 | 58.1 | 46.6 |
| Example No. 4 | 0.3 | 77.2 | 29.1 |
| Example No. 4 | 1.0 | 68.8 | 36.8 |
| Example No. 4 | 3.0 | 60.4 | 44.5 |

| (2) Antiinflammatory effect on the local granuloma sac model | | | |
| --- | --- | --- | --- |
| Compound | Dose (mg/sac) | Exudate (ml) | Inhibition (%) | Thymus involution (%) |
| Control | 0 | 15.3 | 0 | 0 |
| Prednisolone | 1 | 11.7 | 23.6 | 27.2 |
| Prednisolone | 3 | 9.2 | 39.9 | 44.1 |
| Prednisolone | 9 | 5.8 | 62.2 | 55.5 |
| Example No. 3 | 1 | 10.3 | 32.7 | 28.7 |
| Example No. 3 | 3 | 9.2 | 39.9 | 33.1 |
| Example No. 3 | 9 | 3.8 | 74.9 | 37.7 |
| Example No. 4 | 1 | 10.4 | 32.1 | 21.1 |
| Example No. 4 | 3 | 7.5 | 50.8 | 23.8 |
| Example No. 4 | 9 | 5.8 | 62.3 | 33.9 |

It is unambiguously evident from the results of the above investigations that the novel $\Delta^{14}$-16α,17-dihydroxypregnane derivatives of formula (I) according to the invention exert on both models a highly significant local (topical) antiinflammatory activity exceeding that of the reference substance and their harmful systemic effect (thymus involution) is lower than that of prednisolone.

The invention is illustrated in detail by the following non limiting Examples.

EXAMPLE 1

Preparation of 11β,16α,17,21-tetrahydroxypregna-4,14-dien-3,20-dion-21-acetate

A solution containing 1 g (2.588 mmol) of 11β,21-dihydroxypregna-4,16-dien-3,20-dion-21-acetate in 40 ml of glacial acetic acid is cooled to 13° to 15° C. and 0.45 g (2.847 mmol) of potassium permanganate dissolved in 40 ml of water is portionwise added at the same temperature over 5 to 10 minutes. After the addition, the excess of the oxidizing agent is decomposed by adding 0.6 g of sodium pyrosulfite dissolved in 4.0 ml of water to the reaction mixture. After stirring for 15 minutes the reaction mixture is poured into 500 ml of deionized water, stirred for 1 hour, filtered and the precipitate is washed with water up to neutral. After drying the product is recrystallized from ethyl acetate to give 0.48 g (44.3%) of the title compound, m.p.: 220°-225° C.

EXAMPLE 2

Preparation of 11β,16α,17,21-tetrahydroxypregna-1,4,14-trien-3,20-dion-21-acetate 10 g (26.0 mmol) of 11β,21-dihydroxypregna-1,4,16-trien-3,20-dion-21-acetate are dissolved in 400 ml of glacial acetic acid at 15° C., then 4.52 g (28.6 mmol) of potassium permanganate dissolved in 400 ml of water are portionwise added at the same temperature over 5 to 10 minutes. Thereafter, the excess of permanganate is decomposed by adding 5.94 g of sodium pyrosulfite dissolved in 40 ml of water. After stirring for 20 minutes the reaction mixture is poured into 10 liters of water. After stirring for 1 hour the suspension is filtered, washed up to neutral and dried. The crude product obtained is recrystallized from ethyl acetate to give 5.11 g (47.2%) of the title substance, m.p.: 238°-243° C.

EXAMPLE 3

Preparation of 11β,16α,17,21-tetrahydroxypregna-1,4,14-trien-3,20-dion-21-acetate After dissolving 55 g (143.1 mmol) of 11β,21-dihydroxypregna-1,4,16-trien-3,20-dion-21-acetate in 1100 ml of glacial acetic acid, 1650 ml of acetone are added and the solution is cooled between −20° C. and −25° C.

20.35 g (128.8 mmol) of potassium permanganate are dissolved in 440 ml of water, cooled to 0° C. and portionwise added to the above solution of the steroid maintained at −25° C. over 10 to 15 minutes. After 5 minutes the reaction mixture is examined by thin layer chromatography [DC Alufolien Kieselgel 60 $F_{254}$ (Merck) by using a developing system containing chloroform/ether/methanol in 70:30:2 volume ratio and detecting with phosphoric acid]. After about 15 minutes no starting material can be detected in the reaction mixture. The mixture is poured into a solution containing 27 g of sodium pyrosulfite in 27.5 liters of ice-water under stirring. The suspension obtained is stirred at 0° C. for 1 hour, then filtered. The precipitate is washed up to neutral, dried and recrystallized from ethyl acetate to give 36.14 g (60.7%) of the title compound, m.p.: 240°–243° C.

EXAMPLE 4

Preparation of 11β,16α,17,21-tetrahydroxypregna-1,4,14-trien-3,20-dione 0.40 g (2.87 mmol) of potassium carbonate dissolved in 6 ml of water is added to a solution of 2 g (4.78 mmol) of 11β,16α,17,21-tetrahydroxypregna-1,4,14-trien-3,20-dion-21-acetate in 400 ml of methanol under nitrogen. After 15 minutes the pH value of the solution is adjusted to 6.5 by adding acetic acid, the mixture is evaporated to a volume of 15 to 20 ml under reduced pressure and the residue is poured into 500 ml of ice-water. After stirring for 30 minutes the suspension is filtered and the precipitate is dried. The crude product obtained is recrystallized from a 1:3 (volume ratio) mixture of chloroform/methanol to obtain 1.2 g (66.7%) of the title compound, m.p.: 240°–242° C.

EXAMPLE 5

Preparation of 16α,17,21-trihydroxypregna-4,14-dien-3,20-dion-21-acetate 0.53 g (3.373 mmol) of potassium permanganate dissolved in 5 ml of water is portionwise added at 20° C. over 5 minutes to a solution containing 1 g (2.699 mmol) of 21-hydroxypregna-4,16-dien-3,20-dion-21-acetate dissolved in 10 ml of glacial acetic acid at room temperature. After addition, the excess of permanganate is decomposed by adding a solution of 0.72 g of sodium pyrosulfite in 5 ml of water to the reaction mixture, then the mixture is poured into 500 ml of water containing 16.7 g of potassium hydrogen carbonate. After stirring for 1 hour the suspension is filtered, the precipitate is washed with water and dried to give 0.50 g (46.0%) of the title product, m.p.: 215°–220° C.

EXAMPLE 6

Preparation of 16α,17,21-trihydroxypregna-1,4,14-trien-3,20-dion-21-acetate 11 ml of acetone are added to a solution containing 0.35 g (0.95 mmol) of 21-hydroxypregna-1,4,16-trien-3,20-dion-21-acetate in 7 ml of glacial acetic acid and the solution is cooled to a temperature between −20° C. and −25° C. Thereafter, 0.23 g (1.45 mmol) of potassium permanganate dissolved in 2 ml of water is portionwise added at the same temperature. After 15 minutes the reaction mixture is poured into 200 ml of ice-water containing 0.3 g of sodium pyrosulfite. After stirring for 45 minutes the suspension is filtered, the precipitate is washed and dried to obtain 0.20 g (52.6%) of the title compound, m.p.: 220°–223° C.

EXAMPLE 7

Preparation of 9α-fluoro-11β,16α,17,21-tetrahydroxypregna-1,4,14-trien-3,20-dion-21-acetate 1.0 g (2.48 mmol) of 9α-fluoro-11β,21-dihydroxypregna-1,4,16-trien-3,20-dion-21-acetate is dissolved in 20 ml of glacial acetic acid, 30 ml of acetone are added, then the solution is cooled to a temperature between −20° C. and −25° C. A solution containing 0.36 g (2.28 mmol) of potassium permanganate in 10 ml of water is portionwise added at the same temperature. After 20 minutes the reaction mixture is poured into 500 ml of ice-water containing 0.5 g of sodium pyrosulfite. After stirring for 1 hour the suspension is filtered, the precipitate is washed with cold water and dried to give 0.79 g (73.2%) of the title compound, m.p.: 242°–247° C.

EXAMPLE 8

Preparation of 11β,16α,17,21-tetrahydroxypregna-1,4,14-trien-3,20-dion-11-trifluoroacetate-21-acetate After dissolving 5 g (10.41 mmol) of 11β-trifluoroacetoxy-21-acetoxypregna-1,4,16-trien-3,20-dione in a mixture comprising 100 ml of glacial acetic acid and 150 ml of acetone the solution is cooled to a temperature between −20° C. and −25° C., then 1.48 g (9.37 mmol) of potassium permanganate dissolved in 25 ml of water are added at the same temperature. The excess of the oxidizing agent is decomposed by adding 2.0 g of sodium hydrogen sulfite dissolved in 10 ml of water, then the mixture is poured into 2500 ml of ice-water. After stirring for 1 hour the suspension is filtered, the precipitate is washed with a little volume of cold water and dried to give 3.20 g (60.0%) of the title product, m.p.: 119°–124° C.

EXAMPLE 9

Preparation of 11β,16α,17,21-tetrahydroxypregna-1,4,14-trien-3,20-dion-21-benzoate 150 ml of acetone are added to a solution containing 5 g of 11β,21-dihydroxypregna-1,4,16-trien-3,20-dion-21-benzoate in 100 ml of glacial acetic acid, the solution is cooled to a temperature between −20° C. and −25° C. and 1.59 g of potassium permanganate dissolved in 25 ml of water are added at the same temperature. The excess of the oxidizing agent is decomposed by adding 2.5 g of sodium hydrogen sulfite dissolved in 10 ml of water, then the mixture is poured into 2500 ml of ice-water. After stirring for 1 hour the suspension is filtered, the precipitate is washed with a little volume of cold acetone-water mixture and dried to obtain 3.83 g (71.5%) of the title compound, m.p.: 155°–158° C.

The following $\Delta^{14}$-16α,17-dihydroxypregnane derivative of the formula (I) were also prepared as described in Examples 1 to 9: 11β,16α,17,21-tetrahydroxypregna-1,4,14-trien-3,20-dion-21-butyrate; and 11β,16α,17,21-tetrahydroxypregna-1,4,14-trien-3,20-dion-21-caproate.

The compounds of the Formula (I) are furthermore intermediates to prepare compounds of the Formula (III)

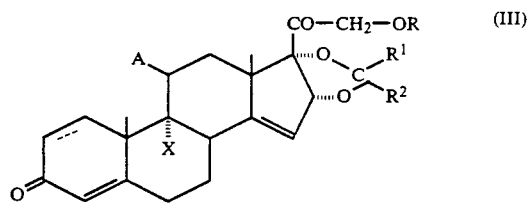

wherein
A stands for hydrogen or hydroxyl group;
X stands for hydrogen or halogen with the proviso that if A is hydrogen, then X also means hydrogen;
R stands for hydrogen, benzoyl or $C_{1-8}$alkanoyl group;

R[1] and R[2], which are the same or different, stand for hydrogen or a $C_{1-4}$alkyl group; or one of R[1] and R[2] is hydrogen and the other is phenyl group; or R[1] and R[2] together form a $C_{4-5}$alkylene group;

means a single or double bond between two adjacent carbon atoms.

The compounds of the Formula (III) are antiinflammatory compounds that are used topically in the same fashion as the present Formula (I) compounds according to Hungarian Patent Application 1155/89.

The Formula (III) compounds are prepared by reacting a compound of the Formula (I) with an oxo compound of the formula (IV),

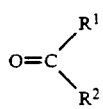

(IV)

wherein R[1] and R[2] are as defined above, in the presence of an acid catalyst.

The following examples show conversion of a compound of the Formula (I) to a compound of the Formula (III).

EXAMPLE 10

Preparation of 11β,16α,17,21-tetrahydroxypregna-4,14-dien-3,20-dion-16,17-cyclic butyraldehyde acetal 0,4 g (0.951 mmol) of 11β,16α,17,21-tetrahydroxypregna-4,14-dien-3,20-dion-21-acetate is dissolved in a mixture containing 0.17 ml (1.90 mmol) of butyraldehyde, 8 ml of acetonitrile and 0.17 ml of 70% perchloric acid. Both the weighing-in and the reaction are carried out under nitrogen. After 10 minutes 4 ml of 5% potassium hydrogen carbonate solution are added to the reaction mixture and the neutralized solution is extracted with ethyl acetate. After drying, the extract is evaporated under reduced pressure. The oily evaporation residue is dissolved in 6 ml of methanol under nitrogen and after adding 0.4 ml of 60% aqueous perchloric acid it is left to stand at room temperature for 10 hours. The mixture is poured into 200 ml of water, the crude product obtained is first recrystallized from a mixture of dichloromethane and n-hexane and then from anhydrous ethanol to obtain 0.35 g (85%) of the title compound.

According to the HPLC (high performance liquid chromatography) analysis the purity of the above product is 98%, m.p.: 96°–101° C.

EXAMPLE 11

Preparation of 11β,16α,17,21-tetrahydroxypregna-1,4,14-trien-3,20-dion-16,17-cyclic butyraldehyde acetal After weighing in 3.5 ml of 70% perchloric acid and 3.5 ml of redistilled butyraldehyde into 160 ml of acetonitrile under dry nitrogen, 8.00 g (0.0191 mol) of 11β,16α,17,21-tetrahydroxypregna-1,4,14-trien-3,20-dion-21-acetate are portionwise added under stirring over 10 minutes. The steroid substance is immediately dissolved. After stirring the solution at room temperature for 30 minutes (the progress of the reaction is observed by using TLC analysis). The reaction mixture is poured into 80 ml of 5% potassium hydrogen carbonate solution and then extracted with 80 ml of ethyl acetate. After washing the extract with water up to neutral and then shaking with concentrated sodium chloride solution it is dried over anhydrous sodium sulfate and evaporated under reduced pressure until it becomes free from the solvent.

After dissolving the evaporation residue in 120 ml of methanol under nitrogen 8 ml of 70% aqueous perchloric acid are dropwise added to the solution. The reaction mixture is stirred at room temperature for 8 hours and then poured into 1600 ml of water. After stirring for 1 hour it is filtered to give 7.95 g (96.59%) of the title compound. This product is purified by suspending in 20 volumes of a 1:5 dichloromethane/n-hexane mixture and recrystallizing from a 1:4 mixture of ethanol and water. In this way a pure title compound is obtained, m.p.: 131°–134° C. (decomposition at 205° C., $[\alpha]_D^{20} = +0.69°$ (dichloromethane. c=1).

IR spectrum ($\nu$, cm$^{-1}$): 3420 (—OH), 1722 (20-oxo). 1657 (3-oxo), 1614 and 1598 (C=C).

EXAMPLE 12

Preparation of 11β,16α,17,21-tetrahydroxypregna-1,4,14-trien-3,20-dion-16,17-cyclic butyraldehyde acetal 0.5 ml of 70% perchloric acid and 0.5 ml of redistilled butyraldehyde are added to 20 ml of acetonitrile under dry nitrogen, then 1.00 g of 11β,16α,17,21-tetrahydroxypregna-1,4,14-trien-3,20-dione is added in little portions during 10 minutes while stirring. The reaction proceeds within 15 minutes. Then the reaction mixture is poured into 2000 ml of water, stirred for 1 hour and filtered. The crude title product thus obtained is purified as described in the preceding Example to obtain 1.05 g (91.8%) of pure title compound, m.p.: 130°–133° C.

EXAMPLE 13

Preparation of 11β,16α,17,21-tetrahydroxypregna-1,4,14-trien-3,20-dion-16,17-cyclic acetaldehyde acetal After introducing 2.2 ml of 70% perchloric acid and 1.3 ml of acetaldehyde into 100 ml of acetonitrile under dry nitrogen, 5.00 g of 11β,16α,17,21-tetrahydroxypregna-1,4,14-trien-3,20-dion-21-acetate are added in several little portions under stirring. The 21-acetoxy derivative of the cyclic acetal is first recovered as described in Example 1 which is then hydrolyzed to give 4.61 g (95.87%) of the title product, m.p.: 169°–173° C.

EXAMPLE 14

Preparation of 11β,16α,17,21-tetrahydroxypregna-1,4,14-trien-3,20-dion-16,17-cyclic benzaldehyde acetal After introducing 2.2 ml of 70% perchloric acid and 2.4 ml of redistilled benzaldehyde into 100 ml of acetonitrile under dry nitrogen, 5.00 g of 11β,16α,17,21-tetrahydroxypregna-1,4,14-trien-3,20-dion-21-acetate are added in several little portions under stirring. The 21-acetoxy derivative of the cyclic acetal is first recovered as described in Example 1 which is then hydrolyzed to obtain 4.92 g (90.99%) of the title compound, m.p.: 228°–233° C.

EXAMPLE 15

Preparation of
11β,16α,17,21-tetrahydroxypregna-1,4,14-trien-3,20-dion-16,17-cyclic isobutyraldehyde acetal 5.0 g of 11β,16α,17,21-tetrahydroxypregna-1,4,14-trien-3,20-dion-21-acetate are dissolved in a mixture containing 100 ml of acetonitrile, 2.2 ml of 70% perchloric acid and 2.2 ml of isobutyraldehyde. Both the weighing-in operations and the reaction are carried out under nitrogen.

The 21-acetoxy derivative of the cyclic acetal is first recovered as described in Example 10 then the 21-acetoxy group is hydrolyzed to result in the free hydroxyl group by using aqueous perchloric acid solution to give 4.97 g (96.68%) of the title compound, m.p.: 132°–136° C. $[\alpha]_D^{24} = +0.607°$ (dichloromethane, c=1).

IR spectrum ($v$, cm$^{-1}$): 3416 (—OH), 1720 (20-oxo), 1657 (3-oxo), 1618 and 1588.

EXAMPLE 16

Preparation of
11β,16α,17,21-tetrahydroxypregna-1,4,14-trien-3,20-dion-16,17-cyclic acetonide 21-acetate 10 g (0.0239 mol) of 11β,16α,17,21-tetrahydroxypregna-1,4,14-trien-3,20-dion-21-acetate are transformed to a paste with 125 ml of acetone under dry nitrogen at room temperature while stirring. Parallelly, 1.6 ml of concentrated sulfuric acid are slowly dropped to 1.0 ml of 70% aqueous perchloric acid under cooling and stirring in an other flask. The anhydrous perchloric acid thus prepared is added to the suspension of the steroid in acetone. The steroid is dissolved within about 10 minutes. After stirring for 2 hours the solution is poured into 1000 ml of 2% sodium hydrogen carbonate solution, stirred for 1 hour and then the precipitate is recrystallized from acetone to result in 10.01 g (91.41%) of the title compound, m.p.: 249°–261° C.

EXAMPLE 17

Preparation of
11β,16α,17,21-tetrahydroxypregna-1,4,14-trien-3,20-dion-16,17-cyclic acetonide 2 g (0.0053 mol) of 11β,16α,17,21-tetrahydroxypregna-1,4,14-trien-3,20-dione are transformed to a paste with 20 ml of acetone under dry nitrogen at room temperature while stirring. To this mixture 1.0 ml of 70% aqueous prechloric acid is added at room temperature under stirring. The reaction proceeds within 30 minutes. After pouring the reaction mixture into 1000 ml of 2% aqueous potassium hydrogen carbonate solution and stirring for 30 minutes, the precipitate is filtered and dried to obtain 2.02 g (91.29%) of the title substance which is recrystallized from acetone, m.p.: 212°–216° C.

EXAMPLE 18

Preparation of
11β,16α,17,21-tetrahydroxypregna-1,4,14-trien-3,20-dion-16,17-cyclic acetonide 1.0 g (0.00218 mol) of 11β,16α,17,21-tetrahydroxypregna-1,4,14-trien-3,20-dion-16,17-cyclic acetonide 21-acetate is transformed to a paste with 100 ml of methanol under nitrogen. To this mixture 0.166 g of potassium carbonate dissolved in 1.1 ml of deionized water is added. The solid phase goes into solution within 5 minutes. After 10 minutes the pH value of the solution is adjusted to 6 by adding 1N hydrochloric acid then the solution is evaporated until it becomes free from solvent. The residue is thoroughly mixed with 100 ml of deionized water, filtered and dried. The product thus obtained is recrystallized from acetone to give 0.79 g (86.98%) of the title compound, m.p.: 210°–215° C.

EXAMPLE 19

Preparation of
11β,16α,17,21-tetrahydroxypregna-1,4,14-trien-3,20-dion-16,17-cyclic acetonide 1.0 g (0.00218 mol) of 11β,16α,17,21-tetrahydroxypregna-1,4,14-trien-3,20-dion-16,17-cyclic acetonide 21-acetate is dissolved in 200 ml of methanol under nitrogen. After adding 2.0 ml of deionized water and 2.0 ml of 60% aqueous perchloric acid the reaction mixture is stirred at room temperature for 48 hours and then evaporated to one tenth of its original volume. After adding 20 ml of deionized water to the evaporation residue and extracting with dichloromethane, the extract is evaporated to dryness and the residue is recrystallized from ether to give 0.85 g (93.6%) of the title compound, 212°–216° C.

EXAMPLE 20

Preparation of
11β,16α,17,21-tetrahydroxypregna-1,4,14-trien-3,20-dion-16,17-cyclic cyclopentanone ketal After adding 0.44 ml of 70% aqueous perchloric acid and 0.43 ml of cyclopentanone to 20 ml of acetonitrile under nitrogen, 1 g of 11β,16α,17,21-tetrahydroxypregna-1,4,14-trien-3,20-dion-21-acetate is added to the solution at room temperature. After stirring the reaction mixture for 8 hours the 21-acetate derivative of the cyclic cyclopentanone ketal is first recovered as described in Example 1 which is then hydrolyzed according to Example 18 to obtain 0.50 g (47.3%) of the title compound, m.p.: 140°–145° C.

EXAMPLE 21

Preparation of
11β,16α,17,21-tetrahydroxypregna-1,4,14-trien-3,20-dion-16,17-cyclic cyclohexanone ketal After adding 0.44 ml of 70% aqueous perchloric acid and 0.75 ml of cyclohexanone to 20 ml of acetonitrile under nitrogen 1 g of 11β,16α,17,21-tetrahydroxypregna-1,4,14-trien-3,20-dion-21-acetate is added to the above solution at room temperature. After stirring the reaction mixture for 30 minutes the 21-acetate derivative of the cyclic cyclohexanone ketal is first recovered as described in Example 20 which is then hydrolyzed according to Example 18 to obtain 0.75 g (68.74%) of the title substance, m.p.: 220°–223° C.

EXAMPLE 22

Preparation of
9α-fluoro-11β,16α,17,21-tetrahydroxypregna-1,4,14-trien-3,20-dion-16,17-cyclic butyraldehyde acetal 0.3 g (0.69 mmol) of 9α-fluoro-11β,16α,17,21-tetrahydroxypregna-1,4,14-trien-3,20-dion-21-acetate is added to a mixture containing 0.13 ml of butyraldehyde, 0.14 ml of 70% aqueous perchloric acid and 30 ml of ethyl acetate. The suspension obtained becomes clear within 30 minutes. After stirring for 1 hour the reaction mixture is worked up as described in Example 10 and the 21-acetate derivative of the cyclic butyraldehyde acetal thus obtained is hydrolyzed by using 0.5 ml of 70% aqueous perchloric acid in 5 ml of methanol according to Example 18. After pouring the reaction mixture into 200 ml of water the precipitate is filtered and dried to obtain 0.24 g (77.9%) of the title compound, m.p.: 130°–136° C.

EXAMPLE 23

Preparation of 11β,16α,17,21-tetrahydroxypregna-1,4,14-trien-3,20-dion-16,17-cyclic butyraldehyde acetal 21-butyrate 1.0 g (2.334 mmol) of 11β,16α,17,21-tetrahydroxypregna-1,4,14-trien-3,20-dion-16,17-cyclic butyraldehyde acetal (prepared according to Example 11) is dissolved in 15 ml of anhydrous pyridine under dry nitrogen, then 0.77 ml (4.668 mmol) of butyric acid anhydride is added at room temperature. The acylation proceeds within 6 to 8 hours. Then the reaction mixture is poured into 500 ml of water containing 17 ml of concentrated hydrochloric acid, stirred for 1 hour and filtered. The precipitate is recrystallized from ethanol and dried to obtain 1.05 g (90%) of the title product, m.p.: 123°–125° C., with an $R_f$ value of 0.50 (developed with a 70:30:2 mixture of chloroform/ether/methanol).

EXAMPLE 24

Preparation of 11β,16α,17,21-tetrahydroxypregna-1,4,14-trien-3,20-dion-16,17-cyclic butyraldehyde acetal 21-caproate 1.0 g (2.334 mmol) of 11β,16α,17,21-tetrahydroxypregna-1,4,14-trien-3,20-dion-16,17-cyclic butyraldehyde acetal (prepared according to Example 11) is dissolved in 15 ml of anhydrous pyridine under dry nitrogen and 1.08 ml of caproic acid anhydride are added at room temperature. Further on Example 16 is followed to give 1.05 g (90%) of the title compound with an $R_f$ value of 0.47 (developed with a 70:30:2 mixture of chloroform/ether/methanol).

We claim:
1. A compound of the formula (I),

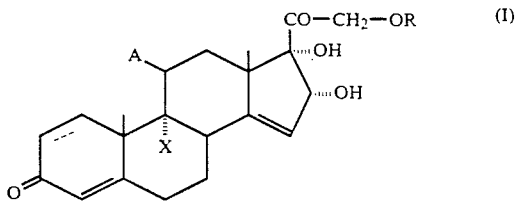

wherein
A stands for hydrogen, hydroxyl or trifluoroacetoxy group;
X stands for hydrogen or halogen with the proviso that if A is hydrogen, then X also means hydrogen;
R stands for hydrogen, benzoyl or $C_{1-8}$alkanoyl group; and
represents a single or double bond between two adjacent carbon atoms.

2. A compound defined in claim 1 selected from the group consisting of
11β,16α,17,21-tetrahydroxypregna-4,14-dien-3,20-dion-21-acetate,
11β,16α,17,21-tetrahydroxypregna-1,4,14-trien-3,20-dion-21-acetate,
16α,17,21-trihydroxypregna-4,14-dien-3,20-dion-21-acetate,
16α,17,21-trihydroxypregna-4,14-dien-3,20-dione,
16α,17,21-trihydroxypregna-1,4,14,-trien-3,20-dion-21-acetate,
9α-fluoro-11β,16α,17,21-tetrahydroxypregna-1,4,14-trien-3,20-dion-21-acetate,
11β,16α,17,21-tetrahydroxypregna-1,4,14-trien-3,20-dion-11-trifluoroacetate-21-acetate, and
11β,16α,17,21-tetrahydroxypregna-1,4,14-trien-3,20-dion-21-benzoate.

3. An antiinflammatory pharmaceutical composition, which comprises as active ingredient a therapeutically effective dose of a compound of the formula (I) as defined in claim 1, in admixture with carriers and/or diluting, stabilizing, pH- and osmotic pressure-adjusting agents and formulating additives commonly used in the pharmaceutical industry.

4. Method for treating mammals suffering from an inflammatory disease, which comprises administering a therapeutically effective amount of a compound of the Formula (I) as defined in claim 1.

5. 11β,16α,17,21-tetrahydroxypregna-1,4,14-trien-3,20-dione-21-acetate as defined in claim 1.

6. 11β,16α,17,21-tetrahydroxypregna-1,4,14-trien-3,20-dione as defined in claim 1.

* * * * *